Feb. 12, 1974 F. W. ANDERSON Plant Pat. 3,476
PEACH TREE
Filed Oct. 6, 1972
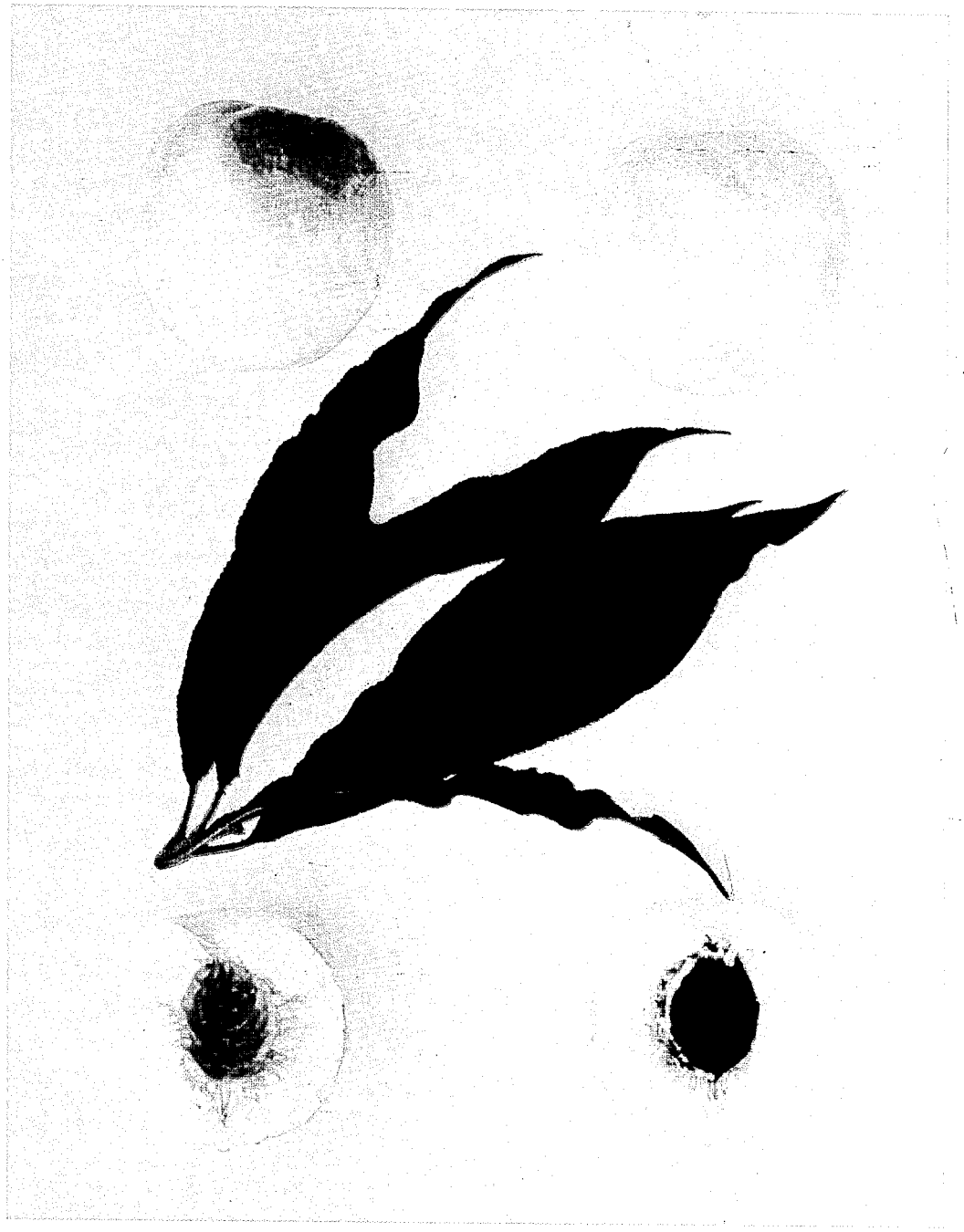

United States Patent Office

Plant Pat. 3,476
Patented Feb. 12, 1974

3,476

PEACH TREE

Frederic W. Anderson, Merced, Calif., assignor to
L. E. Cooke Co., Visalia, Calif.

Filed Oct. 6, 1972, Ser. No. 295,595
Int. Cl. A01h 5/03
U.S. Cl. Plt.—43 1 Claim

ABSTRACT OF THE DISCLOSURE

A genetically dwarf peach tree which is vigorous, spreading, dense, foliated with large leaves having globose glands, and a regular and productive bearer of medium size, globose to slightly oblate, symmetrical, uniform, freestone fruit, having yellow skin partially overspread with red, yellow flesh, and a red pit cavity with the red streaked into the flesh.

Background of the variety: Over a substantial number of years I have engaged in an extensive and continuing plant breeding program at my experimental nursery and orchard located near Le Grand, Merced County, Calif.; one purpose of such program being to provide improved varieties of fruit trees. The present variety of peach tree resulted from my endeavors in the conduct of such plant breeding program.

Origin of the variety: The present variety of genetically dwarf peach tree was originated by me in my experimental nursery and orchard, located as aforesaid, as a first generation ($F_1$) cross between the Golden Glory dwarf peach (U.S. Plant Pat. No. 2,418) as the seed parent, and the Bonanza dwarf peach (U.S. Plant Pat. No, 2,213), as the pollen parent. The variety, as thus originated, and under careful and containing observation, evidenced—upon bearing fruit—certain novel characteristics which were commercially desirable, and I, therefore, undertook asexual reproduction of the variety preparatory to introducing it to the trade.

Asexual reproduction of the variety: Subsequent to origination and selection by me of the present variety of peach tree, in the manner above described, I asexually reproduced it by top-working on mature trees in my said experimental orchard, and in maturity such reproductions ran true to the original tree in all respects.

Summary of the variety: The herein claimed new and distinct variety of genetically dwarf peach tree is vigorous, spreading, dense, foliated with large leaves having globose glands, and a regular and productive bearer of medium size, globose to slightly oblate, symmetrical, uniform, freestone fruit, having yellow skin partially overspread with red, yellow flesh, and a red pit cavity with the red streaked into the flesh.

The herein claimed new and distinct variety of genetically dwarf peach tree, characterized as above, most nearly resembles the Golden Glory, its seed parent, but in particular comparison has larger, firmer, and more attractive fruit. In comparison to the Bonanza, its pollen parent, the herein claimed variety of genetically dwarf peach has leaves with globose glands, and flowers which appear earlier in the season than said Bonanza and most other dwarf peach varieties.

The herein claimed new and distinct variety of genetically dwarf peach tree is also characterized by requiring less winter chilling than either the Golden Glory or the Bonanza.

Brief description of the drawing: The drawing is an illustration, by photographic reproduction in color, of leaves and fruit of the variety; one of the fruit being cut into halves to expose the flesh, with the stone remaining in one such half.

Description of the variety: The bontanical details of this new and distinct variety of peach tree—with color definitions (except those in common color terms) referenced to Maerz and Paul Dictionary of Color—are as follows:

Tree:
- *Type.*—Genetically dwarf.
- *Vigor.*—Vigorous.
- *Growth.*—Spreading.
- *Density.*—Dense.
- *Productivity.*—Productive.
- *Bearing.*—Regular bearer.

Trunk:
- *Size.*—Stocky.
- *Texture.*—*Shaggy.*

Branches:
- *Size.*—Stocky.
- *Texture.*—Shaggy.

Leaves:
- *Size.*—Large. Average length—6". Average width—1¼".
- *Form.*—Acuminate, abruptly pointed.
- *Thickness.*—Medium.
- *Texture.*—Smooth.
- *Margin.*—Grenate, finely serrate.
- *Petiole.*—Short, medium thickness.
- *Glands.*—Average number—2 to 3. Alternate, medium size, globose, Red. Usually positioned 2 on base of blade, sometimes on petiole.
- *Color.*—Top side—Medium green (23–L–8). Under side—Lighter green (22–L–7).

Flower buds:
- *Size.*—Medium.

Flowers:
- *Blooming period.*—Date of first bloom: Feb. 27, 1972. Date of last bloom: Mar. 7, 1972. Early, as compared with other varieties.
- *Size.*—Large.

Fruit:
- *Maturity when described.*—Eating ripe—Aug. 17, 1972.
- *Date of first picking.*—Aug. 1, 1972.
- *Date of last picking.*—Aug. 10, 1972.
- *Size.*—Uniform, medium. Average diameter axially—2¾". Average transversely in suture plane—2⅝".
- *Form.*—Uniform, symmetrical, globose to slightly oblate.
- *Suture.*—Deep. Extends from base over entire circumference. Marked depression beyond pistil point.
- *Ventral surface.*—Rounded strongly. Lipped toward base—apex.
- *Lips.*—Equal.
- *Cavity.*—Circular. Elongated in suture plane with suture showing on one side. Average depth—⅜". Average breadth—¾".
- *Base.*—Truncate.
- *Apex.*—Depressed.

Skin:
- *Thickness.*—Medium.
- *Texture.*—Medium.
- *Tendency to crack.*—None observed.
- *Down.*—Moderate, medium length.
- *Color.*—Yellow (9–L–4) overspread with red (5–K–5 to 5–L–5) on sunny side, with some red streaks and mottling.

Flesh:

*Amygdalin.*—Moderate.
Juice.—Moderate.
*Texture.*—Medium, melting.
*Fibers.*—Abundant, fine, tender.
*Ripens.*—Evenly.
*Flavor.*—Mild.
*Aroma.*—Distinct to wanting.
*Eating quality.*—Fair to good.
*Color.*—Yellow (10–L–5).
*Surface of pit cavity.*—Red (5–K–5) with pink fibers; the red streaking into the flesh from the pit cavity.

Stone:

*Type.*—Free. Parts from flesh smoothly.
*Size.*—Medium. Average length—1⅛". Average breadth—1". Average thickness—11/16".
*Form.*—Globose.
*Base.*—Straight.
*Hilum.*—Oblong.
*Apex.*—Rounded to acute.
*Sides.*—Equal.
*Surface.*—Irregularly furrowed throughout. Ridged throughout.
*Ridges.*—Rounded toward base. Interrupted.
*Pits.*—Elongated.
*Ventral edge.*—Thick. Without wing throughout.
*Dorsal edge.*—Deep, narrow groove toward base to center.
*Tendency to split.*—Slight.
*Color.*—Brown (8–J–9).

Use: Market—local. Culinary.
Keeping quality: Medium.
Resistance to insects and diseases: No unusual susceptibilities noted.
Shipping quality: Medium.

The peach tree and its fruit herein described may vary in slight detail due to climatic and soil conditions under which the variety may be grown; the present dedescription being of the variety as grown in the Central Valley of California.

I claim:

1. A new and distinct variety of genetically dwarf peach tree, substantially as shown and described, which is vigorous, spreading, dense, foliated with large leaves having globose glands, and a regular and productive bearer of medium size, globose to slightly oblate, symmetrical, uniform, freestone fruit, having yellow skin partially overspread with red, yellow flesh, and a red pit cavity with the red streaked into the flesh; the variety most nearly resembling the Golden Glory, its seed parent, but in particular comparison has larger, firmer, and more attractive fruit; the variety, in comparison to the Bonanza, its pollen parent, having leaves with globose glands, and flowers which appear earlier in the season; and the variety requiring less winter chilling than either the Golden Glory or the Bonanza.

No references cited.

ROBERT E. BAGWILL, Primary Examiner